United States Patent [19]

Nappa et al.

[11] Patent Number: 5,274,189
[45] Date of Patent: Dec. 28, 1993

[54] PROCESS FOR THE MANUFACTURE OF LINEAR HYDROFLUOROCARBONS CONTAINING END GROUP HYDROGEN SUBSTITUENTS

[75] Inventors: Mario J. Nappa, Newark, Del.; Allen C. Sievert, Elkton, Md.

[73] Assignee: E. I. Du Pont de Nemours and Company, Wilmington, Del.

[21] Appl. No.: 66,367

[22] Filed: May 24, 1993

[51] Int. Cl.$^5$ .................. C07C 17/16; C07C 19/02
[52] U.S. Cl. .................................. 570/142; 570/134; 570/136
[58] Field of Search .............................. 570/142

[56] References Cited

U.S. PATENT DOCUMENTS

| | | | |
|---|---|---|---|
| 2,666,797 | 5/1950 | Husted et al. | 260/633 |
| 2,980,740 | 4/1961 | Harek et al. | 570/142 |
| 2,993,925 | 7/1961 | Husted | 260/448.8 |
| 3,742,010 | 6/1973 | Hardies et al. | 260/463 |
| 3,799,995 | 3/1974 | Hutchinson | 570/142 |
| 4,346,250 | 8/1982 | Satokawa et al. | 568/842 |
| 4,766,260 | 8/1988 | Manzer et al. | 570/168 |
| 4,902,838 | 2/1990 | Manzer et al. | 570/151 |

FOREIGN PATENT DOCUMENTS

| | | |
|---|---|---|
| 65857/90 | 5/1991 | Australia . |
| 686 | 4/1965 | Japan .................. 570/142 |
| 635083 | 12/1978 | U.S.S.R. .............. 570/142 |
| WO93/02150 | 2/1993 | World Int. Prop. O. . |

OTHER PUBLICATIONS

W. V. Cohen, *J. Org. Chem.* 26:4021–4026 (1961).
Bakhmutov, et al., *Zhur. Org. Khim.* 12(8):1825 (Aug. 1976).
Ashton, et al., *J. Flourine Chem.* 27:263–274 (1985).
Christie, et al., *Aromatic Flourine Compounds IV*, pp. 559–560 (Feb. 1966).
*Chemical Abstracts*, 85:159314g (1976).

*Primary Examiner*—Joseph E. Evans
*Attorney, Agent, or Firm*—Susan Borden Evans

[57] ABSTRACT

This invention relates to a process for producing linear hydrofluorocarbons of the formula $XCF_2(CF_2)_nCH_2F$, where X is H or F, and n is 1 to 7 when X is H, and n is 0 to 7 when X is F, by a vapor phase catalytic reaction of HF and phosgene or sulfuryl chloride with corresponding compounds of the formula $XCF_2(CF_2)_nCH_2OZ$ where Z is H or —C(O)OCH$_2$(CF$_2$)$_n$CF$_2$X.

10 Claims, No Drawings

PROCESS FOR THE MANUFACTURE OF LINEAR HYDROFLUOROCARBONS CONTAINING END GROUP HYDROGEN SUBSTITUENTS

BACKGROUND OF THE INVENTION

This invention relates to a process for producing fluorine-substituted aliphatic hydrocarbons, and more particularly to a process for producing linear hydrofluorocarbons containing end group hydrogen substituents.

There has been recent concern that completely halogenated chlorofluorocarbons may be detrimental toward the Earth's ozone layer. Consequently, there is a world-wide effort to use halogen substituted hydrocarbons which contain fewer chlorine substituents. For example, 1,1,1,2-tetrafluoroethane (HFC-134a), a hydrofluorocarbon which has zero ozone depletion potential is being considered as a replacement for dichlorodifluoromethane (CFC-12) in refrigeration systems. The production of hydrofluorocarbons, (i.e., compounds containing only carbon, hydrogen and fluorine), has been the subject of renewed interest to provide environmentally desirable products for use as solvents, blowing agents, refrigerants, cleaning agents, aerosol propellants, heat transfer media, dielectrics, fire extinguishants and power cycle working fluids (see, e.g., PCT International Publication No. W093/02150).

SUMMARY OF THE INVENTION

A process is provided in accordance with this invention for producing a linear hydrofluorocarbon of the formula $XCF_2(CF_2)_nCH_2F$, wherein X is selected from the group consisting of H and F, and wherein n is an integer from 1 to 7 when X is H and n is an integer from 0 to 7 when X is F. The process comprises the step of reacting $XCF_2(CF_2)_nCH_2OZ$, wherein X and n are as defined above, and wherein Z is selected from the group consisting of H and $—C(O)OCH_2(CF_2)_nCF_2X$, wherein X and n are as defined above, with (i) a compound selected from the group consisting of phosgene and sulfuryl chloride, and (ii) hydrogen fluoride in the vapor phase over a catalyst selected from the group consisting of aluminum fluoride, fluorided alumina, metal supported on aluminum fluoride, metal supported on fluorided alumina, and mixtures thereof at an elevated temperature.

DETAILS OF THE INVENTION

This invention provides a process for producing hydrofluorocarbons of the formula, $CF_3(CF_2)_nCH_2F$, where n is an integer 0 to 7 and of the formula, $HCF_2(CF_2)_nCH_2F$, where n is an integer from 1 to 7. These hydrofluorocarbons are prepared from corresponding alcohols or carbonate esters of said alcohols. Alcohols of the structure, $CF_3(CF_2)_nCH_2OH$, where n is an integer from 0 to 7, can be prepared by known methods using lithium aluminum hydride to reduce the corresponding acids. Alcohols of the structure, $HCF_2(CF_2)_nCH_2OH$, where n is an integer from 1 to 7, can be prepared by known methods by the reaction of methanol and tetrafluoroethylene as described in U.S. Pat. No. 4,346,250 and in Chem. Abst. 85:159314g. The carbonate esters of the above alcohols can be prepared by known methods using phosgene and base.

$XCF_2(CF_2)_nCH_2OY$, where Y equals H or $—C(O)OCH_2(CF_2)_nCF_2X$, is reacted with phosgene or sulfuryl chloride, and HF over a catalyst to produce the following compounds; $HCF_2(CF_2)_nCH_2F$, where n is an integer from 1 to 7, and $CF_3(CF_2)_nCH_2F$, where n is an integer from 0 to 7.

The alcohols or carbonate esters of said alcohols are reacted with HF and either phosgene or sulfuryl chloride over a catalyst comprising aluminum fluoride and/or fluorided alumina. Catalysts which may be used in accordance with this invention include fluorided alumina, aluminum fluoride, metals on aluminum fluoride, and metals on fluorided alumina. Fluorided alumina and aluminum fluoride can be prepared as described in U.S. Pat. No. 4,902,838. Suitable metals for use on the aluminum fluoride or fluorided alumina include chromium, magnesium (e.g., magnesium fluoride), Group VIIB metals (e.g., maganese), Group IIIB metals (e.g., lanthanum), and zinc. In use, such metals are normally present as halides (e.g., fluorides), as oxides, and/or as oxyhalides. Preferably, when supported metals are used, the total metal content of the catalyst is from about 0.1 to 20 percent by weight, typically from about 0.1 to 10 percent by weight. Metals on aluminum fluoride and metals on fluorided alumina can be prepared by procedures described in U.S. Pat. No. 4,766,260. Preferred catalysts include catalysts consisting essentially of aluminum fluoride and/or fluorided alumina.

All references to Groups of the Periodic Table refer to "CAS version" in the Periodic Table of the elements appearing in the CRC Handbook of Chemistry and Physics, 67th Edition, 1986–1987, CRC Press.

Normally, the molar ratio of HF to alcohol or the carbonate ester of said alcohol can range from about 100:1 to about 0.5:1, preferably about 20:1 to 0.75:1, and more preferably about 10:1 to about 1:1.

Generally, the molar ratio of phosgene or sulfuryl chloride to alcohol can range from about 20:1 to about 0.5:1, preferably about 10:1 to 0.75:1, and more preferably about 5:1 to about 1:1.

The reaction of $XCF_2(CF_2)_nCH_2OY$ with HF and phosgene or sulfuryl chloride in the presence of the catalysts of the instant invention is suitably conducted in the vapor phase at a temperature in the range of from about 150° C. to about 425° C., preferably from about 200° C. to about 350° C., and most preferably from about 225° C. to about 275° C. The contact time is typically from about 1 to about 200 seconds, preferably from about 10 to about 100 seconds.

The reaction products may be separated by conventional techniques, such as distillation. Hydrofluorocarbons of the formula $XCF_2(CF_2)_nCH_2F$ likely form azeotropes with HF; and conventional decantation/distillation may be employed if further purification of the hydrofluorocarbons is desired.

The reaction of alcohol with HF and phosgene or sulfuryl chloride may be conducted in any suitable reactor, including fixed and fluidized bed reactors. The reaction vessel should be constructed from materials which are resistant to the corrosive effects of hydrogen fluoride such as Inconel TM nickel alloy and Hastelloy TM nickel alloy.

Pressure is not critical. Atmospheric and superatmospheric pressures (e.g., from about 100 kPa to 7000 kPa) are the most convenient and are therefore preferred.

Hydrofluorocarbons of the formula $XCF_2(CF_2)_nCH_2F$ have numerous uses including applications in compositions used as refrigerants, blowing agents, propellants, cleaning agents, and heat transfer agents.

EXAMPLE 1

$CHF_2CF_2CH_2OH \rightarrow CHF_2CF_2CH_2F$

A 15 in (38.1 cm) × ⅜ in (0.95 cm) Hastelloy ® nickel alloy tube was filled with 8.07 g (about 13 ml) of gamma-alumina ground to 12/20 mesh (1.68/0.84 mm).

A. Catalyst Activation

The catalyst was activated by heating at 175° C. for 35 min. under a nitrogen purge (25 sccm, 4.2×10$^{-7}$ m$^3$/s). HF was fed at 25 sccm (4.210$^{-7}$ m$^3$/s) for 70 min. and a temperature rise to 179° C. was noted. The temperature was raised to 250° C., the HF flow increased to 40 sccm (6.7×10$^{-7}$ m$^3$/s), and the N$_2$ flow decreased to 10 sccm (1.7×10$^{-7}$ m$^3$/s) for 3 hours and 43 minutes. An exotherm to 255° C. was noted. The temperature was raised to 350° C. while maintaining flows for 85 minutes, and then the temperature was raised to 400° C. while maintaining flows for 15 minutes. The flow of HF was reduced to 5 sccm (8.3×10$^{-8}$ m$^3$/s) and the N$_2$ flow to 5 sccm (8.3×10$^{-8}$ m$^3$/s) for 15.3 hours (overnight). The HF was turned off and the N$_2$ flow increased to 200 sccm (3.3×10$^{-6}$ m$^3$/s) for 90 minutes. The HF flow was raised to 40 sccm (6.7×10$^{-7}$ m$^3$/s) and the N$_2$ flow was decreased to 10 sccm (1.7633 10$^{-7}$ m$^3$/s) for 40 minutes; then the temperature was reduced to 250° C. while maintaining the same flows for 25 minutes.

B. Reaction

While the reactor was at 250° C., the flow of CHF$_2$CF$_2$CH$_2$OH was begun at 2.1 sccm (3.5×10$^{-7}$ m$^3$/s), the HF at 7.2 sccm (1.2×10$^{-6}$ m$^3$/s), COCl$_2$ at 3 sccm (5.0×10$^{-7}$ m$^3$/s), and N$_2$ at 2 sccm (3.3×10$^{-7}$ m$^3$/s). The gaseous effluent was analyzed by gas chromatography mass spectroscopy (i.e., GCMS) and found to be 91.5-94.2% CHF$_2$CF$_2$CH$_2$F (HFC-245ca) over a 24 hr period, with no evidence for catalyst deactivation.

$CF_3CF_2CH_2O(CO)OCH_2CF_2CF_3 \rightarrow CF_3CF_2CH_2F$

The catalyst used was prepared and activated as described in Example 1 above. The reactor was cooled to 276° C. The carbonate ester of pentafluoropropanol (CF$_3$CF$_2$CH$_2$O(C=O)OCH$_2$CF$_2$CF$_3$) flow of 1.02 mL/hr (2.0 sccm, 3.3×10$^{-8}$ m$^3$/s), the COCl$_2$ flow of 5.9 sccm (9.8×10$^{-8}$ m$^3$/s), the HF flow of 15.0 sccm (2.5×10$^{-7}$ m$^3$/s), and a N$_2$ flow of 2 sccm (3.3×10$^{-8}$ m$^3$/s) were begun. The gaseous effluent was analyzed by GCMS and found to have 61.8% conversion of organic starting material with a selectivity of 85.1% for CF$_3$CF$_2$CH$_2$F. The flow of COCl$_2$ was lowered to 2.9 sccm (4.8×10$^{-8}$ m$^3$/s) and the HF flow to 7.9 sccm (1.3×10$^{-7}$ m$^3$/s). The gaseous effluent was analyzed by GCMS and found to have 59.5% conversion of organic starting material with a selectivity of 85.4% for CF$_3$CF$_2$CH$_2$F (HFC-236cb).

EXAMPLE 3

$CF_3CH_2OH \rightarrow CF_3CH_2F$

The catalyst used was prepared and activated as described in Example 1 above. The reactor was cooled to 255° C. The trifluoroethanol (CF$_3$CH$_2$OH) flow of 0.46 mL/hr (2.6 sccm, 4.3×10$^{-8}$ m$^3$/s), the COCl$_2$ flow of 3.0 sccm (5.0×10$^{-8}$ m$^3$/s), the HF flow of 6.0 sccm (1.0×10$^{-7}$ m$^3$/s), and a N$_2$ flow of 2 sccm (3.3×10$^{-8}$ m$^3$/s) were begun. The gaseous effluent was analyzed by GCMS and found to be 85.3-88.1% CF$_3$CH$_2$F (HFC-134a) over a 5 hour period with no evidence for catalyst deactivation.

EXAMPLE 4

$CHF_2CF_2CF_2CF_2CH_2OH \rightarrow CHF_2CF_2CF_2CF_2CH_2F$

The catalyst used was prepared and activated as described in Example 1 above. The reactor was cooled to 227° C. The alcohol (CHF$_2$CF$_2$CF$_2$CF$_2$CH$_2$OH) flow of 0.68 mL/hr (2.0 sccm, 3.3×10$^{-8}$ m$^3$/s), the COCl$_2$ flow of 3.0 sccm (5.0×10$^{-8}$ m$^3$/s), the HF flow of 7.0 sccm (1.2×10$^{-7}$ m$^3$/s), and a N$_2$ flow of 2 sccm (3.3×10$^{-8}$ m$^3$/s) were begun. The gaseous effluent was analyzed by GCMS and found to be 94.6-96.3% CHF$_2$CF$_2$CF$_2$CF$_2$CH$_2$F over a 3 hour period with no evidence for catalyst deactivation.

EXAMPLE 5

$CF_3CF_2CH_2OH \rightarrow CF_3CF_2CH_2F$

The same catalyst was used from Example 4 above. The reactor was cooled to 277° C. The alcohol (CF$_3$CF$_2$CH$_2$OH) flow of 0.49 mL/hr (2.0 sccm, 3.3×10$^{-8}$ m$^3$/s), the COCl$_2$ flow of 3.0 sccm (5.0×10$^{-8}$ m$^3$/s), the HF flow of 7.0 sccm (1.2×10$^{-7}$ m$^3$/s), and an N$_2$ flow of 2 sccm (3.3×10$^{-8}$ m$^3$/s) were begun. The gaseous effluent was analyzed by GCMS and found to be 89.3-90.5% CF$_3$CF$_2$CH$_2$F over a 2 hour period with no evidence for catalyst deactivation.

EXAMPLE 6

$CF_3CF_2CF_2CH_2OH \rightarrow CF_3CF_2CF_2CH_2F$

The catalyst used was prepared and activated as described in Example 1 above. The reactor was cooled to 252° C. The alcohol(CF$_3$CF$_2$CF$_2$CH$_2$OH) flow of 0.61 mL/hr (2.0 sccm, 3.3×10$^{-8}$ m$^3$/s), the COCl$_2$ flow of 3.0 sccm (5.0×10$^{-8}$ m$^3$/s), the HF flow of 7.0 sccm (1.2×10$^{-7}$ m$^3$/s), and an N$_2$ flow of 2 sccm (3.3×10$^{-8}$ m$^3$/s) were begun. The gaseous effluent was analyzed by GCMS and found to be 94.8-96.0% CF$_3$CF$_2$CF$_2$CH$_2$F (HFC-338 q) over a 3 hour period with no evidence for catalyst deactivation.

EXAMPLE 7

$CF_3(CF_2)_5CH_2CH_2OH \rightarrow CF_3(CF_2)_5CH=CH_2$

The catalyst used was prepared and activated as described in Example 6 above. The temperature of the catalyst bed was ramped from 225° C. to 275° C. The alcohol (CF$_3$(CF$_2$)$_5$CH$_2$CH$_2$OH) flow of 0.76 mL/hr (2.0 sccm, 3.3×10$^{-8}$ m$^3$/s), the COCl$_2$ flow of 2.8 sccm (4.7×10$^{-8}$ m$^3$/s), the HF flow of 7.0 sccm (1.3×10$^{-7}$ m$^3$/s), and a N$_2$ flow of 2 sccm (3.3×10$^{-8}$ m$^3$/s) were begun. The gaseous effluent was analyzed by GCMS and found to contain 36-44% CF$_3$(CF$_2$)$_5$CH=CH$_2$ as the major product over a 4 hour period with no evidence for catalyst deactivation.

This reaction shows that when the fluoroalcohol contains more than one methylene group between the hydroxyl and fluoromethylene groups elimination to form olefins is the favored reaction.

What we claim is:

1. A process for the preparation of a linear hydrofluorocarbon of the formula XCF$_2$(CF$_2$)$_n$CH$_2$F, wherein X is selected from the group consisting of H and F, and wherein n is an integer from 1 to 7 when X is H and n is an integer from 0 to 7 when X is F, which comprises the step of:

reacting a compound of the formula $XCF_2(CF_2)_nCH_2OZ$, wherein X and n are as defined above, and wherein Z is selected from the group consisting of H and $-C(O)OCH_2(CF_2)_nCF_2X$, wherein X and n are as defined above, with (i) a compound selected from the group consisting of phosgene and sulfuryl chloride, and (ii) hydrogen fluoride, in the vapor phase, over a catalyst selected from the group consisting of aluminum fluoride, fluorided alumina, metal supported on aluminum fluoride, metal supported on fluorided alumina, and mixtures thereof at a temperature of from about 150° to 425° C.

2. A process according to claim 1 wherein the catalyst consists essentially of aluminum fluoride and/or fluorided alumina.

3. A process according to claim 2 wherein the molar ratio of HF to a compound of the formula $XCF_2(CF_2)_nCH_2OZ$ is from about 100:1 to about 0.5:1.

4. A process according to claim 3 wherein the molar ratio of phosgene or sulfuryl chloride to $XCF_2(CF_2)_nCH_2OZ$ is from about 20:1 to about 0.5:1.

5. A process according to claim 4 wherein the temperature is from about 225° C. to about 275° C.

6. A process according to claim 1 wherein the reaction of $XCF_2(CF_2)_nCH_2OZ$ with HF and a compound selected from the group consisting of phosgene and sulfuryl chloride in the presence of the catalyst has a contact time of from about 1 to about 200 seconds.

7. A process according to claim 5 wherein X is H and n is 1.

8. A process according to claim 7 wherein Z is H.

9. A process according to claim 8 wherein $CHF_2CF_2CH_2OH$ is reacted with phosgene and HF to form $CHF_2CF_2CH_2F$.

10. A process according to claim 5 wherein Z is $-C(O)OCH_2(CF_2)_nCF_2X$ and n is 1.

* * * * *

UNITED STATES PATENT AND TRADEMARK OFFICE
CERTIFICATE OF CORRECTION

PATENT NO. : 5,274,189

DATED : December 28, 1993

INVENTOR(S) : Mario J. Nappa and Allen C. Sievert

It is certified that error appears in the above-identified patent and that said Letters Patent is hereby corrected as shown below:

Column 4, line 44, change "EXAMPLE 7" to --COMPARATIVE EXAMPLE A--.

Signed and Sealed this

Sixth Day of September, 1994

Attest:

BRUCE LEHMAN

*Attesting Officer*     *Commissioner of Patents and Trademarks*